United States Patent [19]

Motier

[11] 4,369,141

[45] Jan. 18, 1983

[54] PROCESS TO IMPROVE ISOCYANATE YIELD UPON PYROLYSIS OF A POLYFUNCTIONAL URETHANE WHICH HAS BEEN EXTRACTED WITH A COMBINATION OF HYDROCHLORIC ACID AND ALCOHOL

[75] Inventor: John F. Motier, Glen Mills, Pa.

[73] Assignee: Atlantic Richfield Company, Los Angeles, Calif.

[21] Appl. No.: 295,951

[22] Filed: Aug. 24, 1981

Related U.S. Application Data

[63] Continuation-in-part of Ser. No. 180,799, Aug. 25, 1980, abandoned.

[51] Int. Cl.$^3$ .................. C07C 118/00; C07C 125/07
[52] U.S. Cl. ................................. 260/453 P; 560/25
[58] Field of Search ..................................... 260/453 P

[56] References Cited

U.S. PATENT DOCUMENTS

| | | | |
|---|---|---|---|
| 2,946,768 | 7/1960 | Klauke et al. | 560/25 X |
| 3,919,279 | 11/1975 | Rosenthal et al. | 260/453 P |
| 3,962,302 | 6/1976 | Rosenthal et al. | 260/453 P |
| 4,146,727 | 3/1979 | Shawl et al. | 260/453 P X |
| 4,162,362 | 7/1979 | Shawl et al. | 560/25 |
| 4,172,948 | 10/1979 | Shawl | 260/453 P X |
| 4,287,132 | 9/1981 | Mameniskis et al. | 260/453 P |
| 4,290,968 | 9/1981 | Leonard | 260/453 P |
| 4,292,254 | 9/1981 | Leonard | 260/453 P |

*Primary Examiner*—Joseph Paul Brust
*Attorney, Agent, or Firm*—Delbert E. McCaslin

[57] ABSTRACT

In the process of producing polyisocyanates by (a) condensing an alkyl-N-phenylcarbamate having 1 to 3 carbons in the alkyl moiety with formaldehyde, paraformaldehyde a formaldehyde forming compound such as trioxane in the presence of an acid to produce a condensate containing a mixture of diphenylmethane dicarbamates and polymethylene polyphenyl carbamates with by-product N-benzyl compounds, rearranging said N-benzyl compounds in said condensate with acid catalyst to obtain a pyrolysis feed mixture containing a mixture of diphenylmethane dicarbamates and polymethylene polyphenyl carbamates with by-product amine and amine salts, and (b) thermally decomposing the carbamate moieties in the pyrolysis feed mixture to isocyanate moieties to produce a polyisocyanate mixture of diphenylmethane diisocyanates and polymethylene polyphenyl isocyanates, the improvement comprises increasing the percent isocyanate content of said polyisocyanates by prior to step (b) removing the amine and amine salt by-products by extracting the pyrolysis feed mixture with a solution of an alkanol having 1 to 4 carbon atoms in the alkyl moiety and aqueous hydrochloric acid, and then removing the alcohol-hydrochloric acid extract.

3 Claims, No Drawings

PROCESS TO IMPROVE ISOCYANATE YIELD UPON PYROLYSIS OF A POLYFUNCTIONAL URETHANE WHICH HAS BEEN EXTRACTED WITH A COMBINATION OF HYDROCHLORIC ACID AND ALCOHOL

CROSS REFERENCE TO RELATED APPLICATIONS

This application is a continuation-in-part application of co-pending application Ser. No. 180,799, filed Aug. 25, 1980, now abandoned and entitled PROCESS TO IMPROVE ISOCYANATE YIELD UPON PYROLYSIS OF A POLYFUNCTIONAL URETHANE WHICH HAS BEEN EXTRACTED WITH A COMBINATION OF HYDROCHLORIC ACID AND ALCOHOL.

FIELD OF THE INVENTION

The present invention relates to an improvement in the process for the preparation of polyisocyanates from polycarbamates (polyurethanes). The improvement relates to removal of amine and amine salts from the polyurethane prior to its pyrolytic decomposition to polyisocyanate which results in higher levels of isocyanate content.

BACKGROUND OF THE INVENTION

Polymeric aromatic carbamic acid esters (polyurethanes) such as diphenylmethane dicarbamates particularly the diethyl ester thereof, and the related higher homologs, polymethylene polyphenyl carbamates, ethyl esters thereof have become increasingly important products particularly, for use in the preparation of the commercially valuable diphenylmethane diisocyanates and mixtures of diisocyanates and the polymethylene polyphenyl isocyanates by the decomposition of such polymeric aromatic carbamic acid esters in a suitable solvent as shown in Rosenthal et al., U.S. Pat. Nos. 3,962,302, June 8, 1976 and 3,919,279, Nov. 11, 1975 incorporated herein by reference.

A proposed prior art process for the preparation of polymeric aromatic carbamic acid esters (polyurethanes) is disclosed in Klauke et al., U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce along with desired polyurethanes, varying amounts, i.e., generally between 15 percent and 50 percent by weight, the undesirable N-(alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired "N-benzyl" compounds, which cannot be converted to an isocyanate by pyrolysis, and polyurethanes presents many problems. However, the undesired N-benzyl compounds may be catalytically rearranged to a desired polyurethane in accordance with the teachings of Shawl et al., U.S. Pat. No. 4,146,727, Mar. 27, 1979 and incorporated herein by reference. Accordingly, a product mixture from a condensation as disclosed in aforementioned U.S. Pat. No. 2,946,768 containing diurethanes and polyurethanes, N-benzyl compounds, unreacted alkylphenylcarbamates and other by-products such as amines may be contacted at temperatures of from about 50° C. to 170° C. with a protonic acid medium having a strength at least equal to a 75 percent sulfuric acid such as concentrated sulfuric acid or an acid medium comprising a Lewis acid having a concentration of at least 0.5 percent by weight based on the total reaction mixture, while maintaining a minimum amount of water in the system, to catalytically convert or rearrange said N-benzyl compounds to mono and dicarbamates and polymethylene polyphenyl carbamates.

Shawl, U.S. Pat. No. 4,172,948, Oct. 30, 1979, incorporated herein by reference, discloses a similar rearrangement of N-benzyl compounds which may be achieved by use of anhydrous hydrogen chloride under super atmospheric pressure.

Condensation of aryl carbamic acid esters especially ethylphenylcarbamate using formaldehyde, paraformaldehyde or trioxane may also be conducted with organic sulfonic acids. Shawl, U.S. Pat. No. 4,162,362, July 24, 1979, incorporated herein by reference, teaches that condensation in the presence of an organic sulfonic acid helps eliminate formation of N-benzyl compounds and suppresses certain other undesirable side reactions.

SUMMARY OF THE INVENTION

The acid catalyzed condensation of N-aryl carbamates and the acid rearrangement of N-benzyl compounds produce some hydrolysis of urethane groups to amino groups. Thus, for example, in the acid catalyzed condensation of ethyl-N-phenyl carbamate with formaldehyde some hydrolysis of the urethane (carbamate) groups occur and the amino compound would thus correspond to the carbamate from which it is derived. Such by-product amines are methylene bridged phenyl moieties with each phenyl having a carbamate or amino substituent.

By-product amino compounds may be present in the condensation product as free amines and as amine/acid salts. When the by-product amines and amine salts accompany the polyurethane condensate to its pyrolytic decomposition to polyisocyanate, a significant detrimental effect arises. For example, the amines and amine salts can react with isocyanate groups as they form to produce ureas or biurets. Additionally such undesirable ureas might at elevated temperatures catalyze isocyanate reactions to produce other unwanted by-products such as carbodiimides and isocyanurates.

According to the present invention, those detrimental by-products may be avoided by removing the by-product amines and amine salts by treatment of the carbamate condensation-rearrangement product with hydrochloric acid and a monohydric alkanol having 1 to 4 carbon atoms in the alkyl moiety. Typically, the carbamate condensation-rearrangement product mixture is extracted with a mixture of aqueous hydrochloric acid in ethanol prior to pyrolysis.

Accordingly it is an object of this invention to provide a process with increased yield of polyisocyanates from polyurethanes by removing amines and amine salts from the polyurethane prior to pyrolytic decomposition.

It is another object of this invention to provide a process for producing polyisocyanates with an increased percentage of isocyanate group content.

These and other objects and advantages of this invention will become apparent from the description of the invention which follows and from the claims.

DESCRIPTION OF THE INVENTION

Condensation of alkyl-N-aryl carbamates with formaldehyde is known to yield polyfunctional carbamates (a mixture of diphenylmethane dicarbamates 2,2'; 2,4' and 4,4' diethyl esters thereof and the polymethylene polyphenyl, ethyl esters thereof, when ethyl phenyl carbamate is condensed) with alternating methylene moieties and N-aryl carbamate moieties as shown by the formula

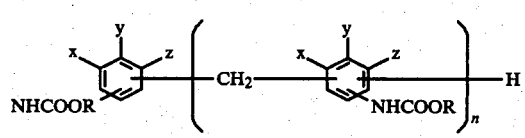

wherein x, y and z when the same are each hydrogen or when different x, y and z may be hydrogen, alkyl having 1-3 carbon atoms, —NHCOOR, —CH$_2$ArNHCOOR, or —N(COOR)CH$_2$Ar;

n is at least one;

R is alkyl having 1-3 carbon atoms and

Ar is phenyl which is unsubstituted or substituted with alkyl having 1-3 carbon atoms.

Production of polyfunctional carbamates by acidic condensation of a monofunctional N-aryl carbamate with formaldehyde results in a small amount of the carbamate functional groups being hydrolyzed to amino groups as shown by the reaction

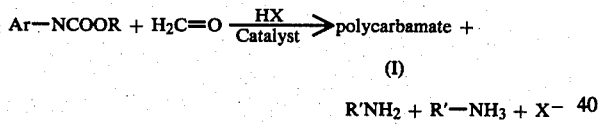

wherein Ar and R are as defined above, the polyfunctional carbamate formula (I), above, and R' is an organic moiety containing methylene bridged aromatic rings bearing carbamate or additional amino substituents. The amino by-products are not desirable and even though their presence is at low levels of concentration (usually in the range of 0.02 to 1.0 weight percent amino) they have a significant detrimental effect of lowering the percentage isocyanate content when the polyfunctional carbamate is pyrolyzed to the corresponding polyisocyanate.

The particular amines which are most troublesome are generally those of higher molecular weights. Because of the high molecular weight, those amines have relatively low distribution coefficients and hence cannot be effectively extracted from the organic medium mixture. Extraction with concentrated strong acids has been found to remove some of the by-product amine. However, amine removal is only partial and a sufficient amount of by-product amine remains to cause a significant detrimental effect in the subsequent pyrolysis step.

It has now been found, quite unexpectedly, that by-product amine can be efficiently removed from the polycarbamate condensation-rearrangement reaction product mixture by extracting the mixture using a combination of monohydric alkanol having 1 to 4 carbon atoms in the alkyl moiety and 15 percent to 37 percent aqueous hydrochloric acid. The effectiveness of the combined alcohol hydrochloric acid as an extraction medium is quite surprising because extraction with alcohol alone has no effect while extraction with aqueous hydrochloric acid alone has only a moderate effect. Use of a combination of alcohol and acid results in a synergistic improvement in the quality of the polycarbamate condensation-rearrangement reaction product and leads to an improved polyisocyanate product from the pyrolysis step.

The procedure for conducting the purification according to this invention is to extract the organic polycarbamate (a mixture of diphenylmethane dicarbamates and polymethylene polyphenyl carbamates) solution at about ambient temperature (approximately 25° C.-30° C.) under atmospheric pressure with a mixture of alcohol-aqueous hydrochloric acid. The ratio of alcohol to acid is about 0.2 to 1.5 parts of alcohol by weight to each part of hydrogen chloride by weight in solution. Extraction is carried out over a short period of time with about 1 to 60 minutes usually being sufficient. Also, whereas ambient temperature is preferred for the extraction, higher or lower temperatures may also be employed.

The polycarbamate solution to be extracted typically contains about 50 percent by weight of polyfunctional carbamates. Nitrobenzene is the usual solvent and in order to accelerate the separation of the alcohol/acid extract from the nitrobenzene solution, toluene or some other aromatic solvent may be added to the nitrobenzene solution. Toluene or other aromatic solvent in an amount up to 300 percent by weight of the nitrobenzene solution may be used.

The ratio of extraction solution to organic mixture being extracted is about 0.2 to 3.0 parts by weight of alcohol/hydrochloric acid solution per part by weight of solution being extracted.

The specific alcohols contemplated are methanol, ethanol, propanol and butanol with ethanol being preferred.

The following examples are provided to illustrate the invention in accordance with the principles of this invention but are not to be construed as limiting the invention in any way except as indicated by the appended claims.

EXAMPLE 1

Preparation of a Polyfunctional Urethane

A polyfunctional urethane condensation product principally comprising a mixture of diphenylmethane dicarbamates, diethyl esters thereof, and polymethylene polyphenyl carbamates, ethyl esters thereof, was prepared from ethyl-N-phenyl carbamate and formaldehyde (in the form of formaldehyde forming trioxane). For ease of handling, the ethyl-N-phenyl carbamate was first dissolved in nitrobenzene to a 50 percent W/W solution. Trioxane was then added at ambient temperature (25° C.). The molar ratio of ethyl-N-phenyl carbamate to formaldhyde was 1.85:1.0. To this solution was added gradually methane sulfonic acid in a molar ratio of acid to carbamate of 1.22:1.0. The resulting exotherm was controlled to less than 80° C., by cooling and controlling the addition of the acid. When all the acid had been added, the reaction mixture was heated at 80° C. for 50 minutes. Then an amount of water equal in weight to the added acid was added, the layers separated and the organic phase washed with water until a pH of 5 was obtained. In order to facilitate the separation of phases in the subsequent extraction, the organic phase was diluted with an equal weight of toluene.

EXAMPLE 2

Pyrolysis of the Polyfunctional Urethane

A portion of the condensate from Example 1 was isolated from the nitrobenzene solution prior to the toluene addition using vacuum distillation. It was dissolved at a 4 percent (W/W) concentration in diphenyl ether at ambient temperature. The solution was heated to diphenyl ether reflux with a nitrogen purge in order to remove liberated ethanol. To catalyze the pyrolysis, 10 ppm of iron in the form of the acetylacetonate salt was added. After 80 minutes at reaction temperature, the pyrolyzed solution was cooled to approximately 100° C. and then vacuum distilled to remove the diphenyl ether. The isolated product had a solvent free isocyanate value of 30.3 weight percent NCO.

EXAMPLE 3

Extraction of the Polyfunctional Urethane with Alcohol Alone

The condensate from Example 1 was diluted with an equal weight of toluene. It was then extracted two times with an equal weight of 20 weight percent ethanol in water. This concentration of alcohol in water represents the ratio of these components present in the combination extraction but omitting the HCl. The resulting washed condensate was isolated by vacuum distillation and was pyrolyzed according to the procedure outlined in Example 2. The isolated polyfunctional isocyanate had a free isocyanate value of 30.3 weight percent NCO. Thus the extraction with alcohol alone had no effect.

EXAMPLE 4

Extraction with Concentrated HCl Alone

The condensate solution from Example 1, having been diluted with an equal weight of toluene, was extracted two times with an amount of 37 percent aqueous hydrochloric acid equal to the weight of the total organic phase. After isolation of the condensate by vacuum distillation, it was pyrolyzed according to the procedure in Example 2. The isolated product had an improved isocyanate value of 30.6 weight percent NCO.

EXAMPLE 5

Extraction with a Combination of Alcohol and Acid

The condensate solution from Example 1 after dilution with an equal amount of toluene was extracted 2 times with an amount of 37 percent aqueous HCl equal to the weight of the combined organic phases. In addition the aqueous HCl was diluted with 1/6 of its weight with ethanol. The ethanol was added in each extraction. After isolation of the condensate and pyrolysis according to the procedure in Example 2, the isolated product had a free isocyanate value of 31.1 weight percent NCO, significantly higher than that obtained from the unextracted condensate as well as that extracted with hydrochloric acid by itself.

EXAMPLE 6

A Polyfunctional Urethane from a Synthetic Ethyl-N-Phenyl Carbamate

A so-called synthetic ethyl-N-phenyl carbamate was prepared from phenyl isocyanate and ethanol. The condensation of this material with formaldehyde was carried out in exactly the same manner as that used in Example 1. The condensate was isolated by vacuum distillation and pyrolyzed according to the procedure in Example 2. The isolated product had a free isocyanate value of 31.0 weight percent NCO.

EXAMPLE 7

Extraction with Hydrochloric Acid Alone

The condensation product from Example 6 was extracted with 37 percent aqueous hydrochloric acid in the manner outlined in Example 4. It was subsequently pyrolyzed according to the procedure in Example 2. The isolated product had a free isocyanate value of 31.0 percent NCO, exactly that which was found for the unextracted condensate.

EXAMPLE 8

Extraction with a Combination of Alcohol and Hydrochloric Acid

The condensation product from Example 6 was extracted with a combination of hydrochloric acid and ethanol in the manner depicted in Example 5. The amount of the various reagents and the condensate were the same as used in Example 5. After pyrolysis according to the procedure of Example 2, the isolated product had a free isocyanate value of 31.5 percent NCO, obviously a significant improvement over that obtained from the condensate itself as well as an acid extracted condensate.

EXAMPLE 9

Example 5 employing condensate of Example 1 was repeated using methanol and N-butanol, respectively, in place of ethanol. After isolation and pyrolysis of the condensate according to the procedure of Example 2, the isolated pyrolysis products had a free isocyanate value of 31.3 and 31.2, respectively.

I claim:

1. In a process for the preparation of a mixture of diphenylmethane diisocyanates and polymethylene polyphenyl isocyanates by
   (a) condensing ethyl-N-phenylcarbamate with formaldehyde in the presence of an acid to produce a condensate containing a mixture of diphenylmethane dicarbamates, diethyl esters thereof, and polymethylene polyphenyl carbamates, ethyl esters thereof, with by-product N-(alkoxycarbonyl)-phenylaminomethylphenyl compounds, rearranging said N-(alkoxycarbonyl)phenylaminomethylphenyl compounds in said condensate with acid catalyst to obtain a pyrolysis feed mixture containing diphenylmethane dicarbamates, diethyl esters thereof, and polymethylene polyphenyl carbamates, ethyl esters thereof, with by-product amine and amine salt compounds resulting from the condensation and rearrangement, and
   (b) thermally decomposing the carbamate moieties in the pyrolysis feed mixture to produce diphenylmethane diisocyanates and polymethylene polyphenyl isocyanates, the improvement which comprises increasing the percent isocyanate content of said diphenylmethane diisocyanates and polymethylene polyphenyl isocyanates by prior to step (b) removing the amine and amine salt by-products by extracting the pyrolysis feed mixture at atmospheric pressure and at about ambient temperature for a period of from about 1 to 60 minutes with a solution of a monohydric alkanol having from 1 to 4 carbon atoms in the alkyl moiety and 15 to 37 percent aqueous hydrochloric acid, said alkanol to hydrochloric acid ratio being from about 0.2 to 1.5 parts of alkanol to each part of hydrogen chloride by weight in solution, said extraction solution being between about 0.2 to 3.0 parts by weight of alkanol and hydrochloric acid per part by weight of pyrolysis feed mixture, and then removing the alcohol-hydrochloric acid extract.

2. The process according to claim 1 wherein said alkanol is ethanol.

3. The process according to claim 1 wherein said hydrochloric acid is 37 percent aqueous hydrochloric acid.

* * * * *